United States Patent [19]

Hassel et al.

[11] Patent Number: 5,193,771
[45] Date of Patent: Mar. 16, 1993

[54] TYPIST'S WRIST SUPPORT

[75] Inventors: H. Charles Hassel, Los Angeles; Neil Nagy, San Pedro, both of Calif.

[73] Assignee: MicroComputer Accessories, Inc., Los Angeles, Calif.

[21] Appl. No.: 750,654

[22] Filed: Aug. 27, 1991

[51] Int. Cl.⁵ .............................................. B43L 15/00
[52] U.S. Cl. .................................................... 248/118
[58] Field of Search .................. 248/118, 118.1, 118.3, 248/118.5, 205.2, 918

[56] References Cited

U.S. PATENT DOCUMENTS

| | | | |
|---|---|---|---|
| D. 270,556 | 3/1877 | Taylor | 248/118.5 |
| 188,984 | 9/1983 | Kneisley | D21/233 |
| 986,620 | 3/1911 | Ballou | 248/118.5 |
| 1,221,513 | 4/1917 | Coyne . | |
| 1,235,199 | 7/1917 | Gavin . | |
| 1,257,846 | 2/1918 | Gregory . | |
| 1,280,158 | 10/1918 | Cardwell . | |
| 1,351,378 | 8/1920 | Frankel . | |
| 1,469,315 | 10/1923 | Hansard . | |
| 2,910,259 | 10/1959 | Johnson | 248/118 |
| 3,295,518 | 1/1967 | Hazlewood | 248/118 |
| 3,496,573 | 2/1970 | Kuchar et al. | 2/161 |
| 3,703,894 | 11/1972 | Galloway et al. | 128/77 |
| 3,724,456 | 4/1973 | Waxman | 128/133 |
| 3,776,225 | 12/1973 | Lonardo | 128/77 |
| 4,183,098 | 1/1980 | Knowles, Jr. | 2/16 |
| 4,259,949 | 4/1981 | Axelsson | 248/118 X |
| 4,294,237 | 10/1981 | Frazier | 128/77 |
| 4,374,439 | 2/1983 | Norman | 2/161 |
| 4,456,002 | 6/1984 | Barber et al. | 128/77 |
| 4,479,648 | 10/1984 | Alivo, Jr. | 273/54 |
| 4,531,241 | 7/1985 | Berger | 2/161 |
| 4,662,364 | 5/1987 | Viegas et al. | 128/87 |
| 4,716,892 | 1/1988 | Brunswick | 128/77 |
| 4,765,319 | 8/1988 | Finnieston et al. | 128/87 |
| 4,784,120 | 11/1988 | Thomas | 248/118 X |
| 4,809,366 | 3/1989 | Pratt | 2/170 |
| 4,831,997 | 5/1989 | Greene | 124/35 |
| 4,840,168 | 6/1989 | Lonardo | 128/77 |
| 4,854,309 | 8/1989 | Elsey . | |
| 4,941,460 | 7/1990 | Working | 128/7 |

FOREIGN PATENT DOCUMENTS

| | | |
|---|---|---|
| 57540 | 7/1819 | Fed. Rep. of Germany . |
| 306715 | 4/1917 | Fed. Rep. of Germany . |
| 104295 | 3/1917 | United Kingdom . |
| 111276 | 11/1917 | United Kingdom . |

Primary Examiner—Alvin C. Chin-Shue
Attorney, Agent, or Firm—Price, Gess & Ubell

[57] ABSTRACT

The present invention relates to a wrist support that is designed to maintain a typist's hand, wrist, and forearm in a neutral or aligned position. The wrist support includes a base member having an upper curved surface that partially conforms to the typist's wrist. The base member is preferably fastened to the user's wrist with a flexible strap having a plurality of hook and loop pile patches. An arm extends forward and upward from a front edge of the base member and has a support member at a distal end thereof. The support member is positioned under the user's palm to lightly support the user's hand without unduly restricting movement of the user's fingers. The support member preferably has an upper curved surface that is large enough to comfortably support the user's palm, but small enough so that the user may pivot his or her fingers up or down, backwards and forwards.

7 Claims, 3 Drawing Sheets

TYPIST'S WRIST SUPPORT

BACKGROUND OF THE INVENTION

1. Field of the Invention

The present invention relates generally to wrist braces and, more particularly, to a wrist support for a typist that supports the typist's palm while allowing upward and forward movement of the typist's hand and unrestricted movement of the typist's fingers.

2. Description of Related Art

Computer users and ten-key operators must type in data for extended periods of time and, therefore, have become more and more concerned with comfort. There are literally hundreds of products available on the market to help increase the comfort of the extended typist. For example, there are various keyboard support devices which allow the keyboard to be variably located at any desired height. There are also devices which allow the user to support his or her wrists on cushioned pads and at variable heights relative to the keyboard. There are even comprehensive carefully designed work stations that include chairs and work surfaces designed to maintain the user's forearm and wrist at the proper height and orientation relative to the keyboard. The alignment of a user's hand, wrist, and forearm is commonly called the "neutral wrist position." The general purpose of all of the foregoing devices is to help the user maintain the neutral wrist position and thereby reduce discomfort normally associated with extended typing or keying.

While the foregoing devices are helpful, they are typically quite expensive. Moreover, the just described devices are not portable and essentially limited to use with an ordinary keyboard permanently located at a single work station. With the advent of the portable computer, a need has developed for a portable typist's wrist support. Moreover, there is a need for a wrist support that is effective for a ten-key typist.

There are innumerable wrist braces on the market for various medical and sports related concerns. However, most of the known wrist braces immobilize the wearer's fingers, wrist or both. There continues to be a need for a wrist support which will support a typist's palm in an appropriate position, but still allow the typist to extend his or her wrist forward and to move his or her fingers independent of the palm support.

SUMMARY OF THE INVENTION

It is an object of the present invention to provide a typist's wrist support that overcomes the problems associated with large immobile work station devices.

In particular, it is an object of the present invention to provide a wrist support comprised of a base member, an arm that extends forward from a front edge of the base member and a support member having an upper curved surface attached to a distal end of the arm for engaging a user's palm from below. The wrist support further comprises means for detachably securing the base member to a user's wrist, which attachment means is preferably comprised of a flexible strap having a loop and pile structure allowing the straps to be wrapped around a user's wrist of any size. The upper surface of the support member preferably has a smooth concave shape and the arm preferably extends upwardly away from the base member at an acute angle. The support member should be large enough to comfortably support the user's palm, but small enough so that the user may pivot his or her fingers up or down. The base member, arm and support member are preferably integrally formed of plastic from a conventional molding operation.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying

DETAILED DESCRIPTION OF THE PREFERRED EMBODIMENT

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide a typist's wrist support.

Figure 1:
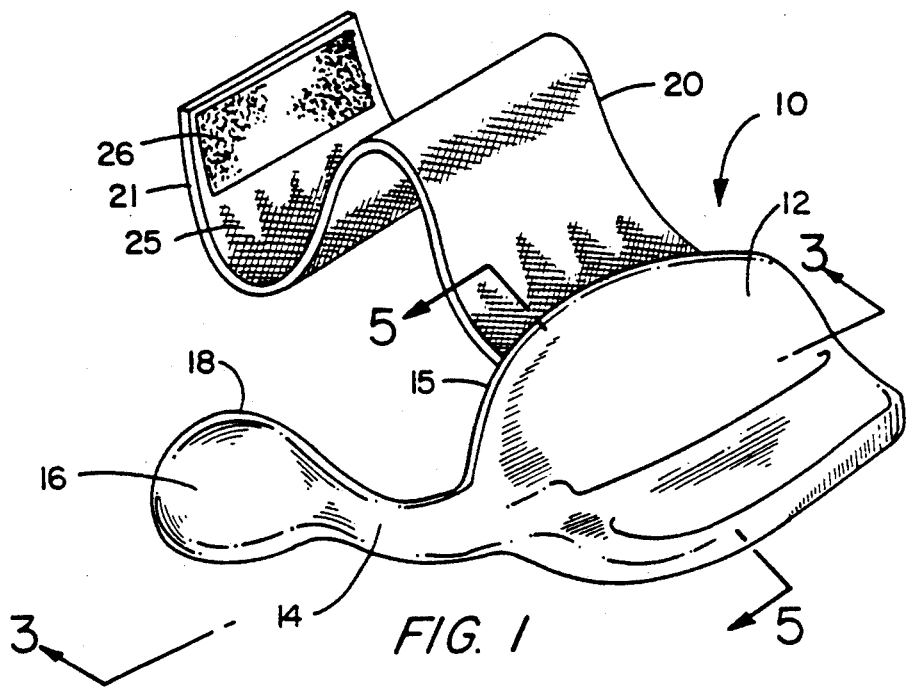
FIG. 1 is a perspective view of a preferred typist's wrist support in accordance with the present invention.

FIG. 1 depicts a preferred wrist support 10 according to the present invention which is comprised of a base member 12, an arm 14 and an appendage or support member 16. The base member 12 preferably has a curved cross-section perpendicular to its long axis such that an upper surface 17 of the base member may wrap partially around a typist's wrist 44. The base member 12 preferably has a bottom surface 13 that also has a curved cross-section perpendicular to its long axis so that the user may pivot his or her wrists from side to side. However, in the longitudinal direction, the bottom surface 13 is substantially flat and is of sufficient length to substantially inhibit the base member from rocking back and forth relative to the axial direction of the user's arm.

The arm 14 extends forward and acutely upward from a front edge 15 of the base member 12. Because the arm 14 extends acutely upward from the plane of the base member 12, the support member 16 is positioned to lightly support the user's palm. The arm 14 constitutes a rigid support means for supporting the support member 16 forward of the base member 12.

The support member 16 preferably has a smooth upper surface 18 that is comfortable when pressed against the palm. The upper curved surface 18 is preferably convex to form a substantially hemispherical support for the user's palm. The radius of the upper surface 18 should be large enough to comfortably support the user's palm, but small enough to allow the user to freely move his or her fingers. It is readily understood that there are various other possible configurations for the support member 16 that are within the scope of the present invention.

Figure 5:
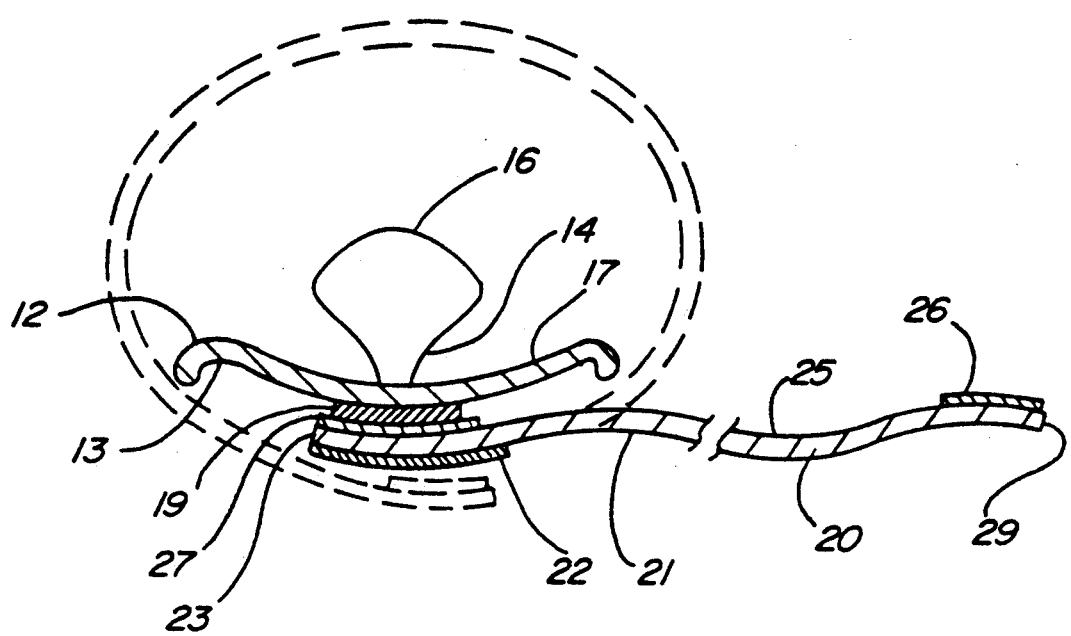
FIG. 5 is a cross-sectional view of the preferred wrist support of FIG. 1 taken along section lines 5—5.

The preferred wrist support 10 is further comprised of means for detachably securing the base member 12 to the user's wrist 44. The preferred means for detachably securing is comprised of a single flexible strap 20 extending from the bottom surface 13 of the base member 12. As shown in FIG. 5, the flexible strap 20 has first and second ends 23, 29. A patch of hook pile material 22 is stitched to an outside surface 21 of the first end 23, and a mating patch of loop pile material 26 is stitched to an inside surface 25 at the second end 29. By this arrangement, the hook and loop pile patches 22, 26 may engage one another and thereby firmly secure the flexible strap 20 around the user's wrist as suggested by the dashed lines of FIG. 5.

Figure 6:
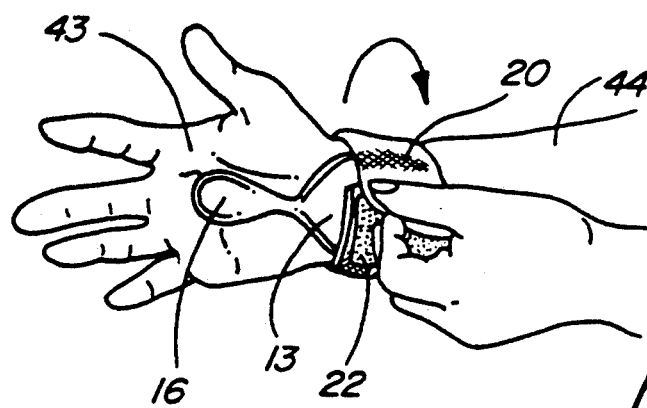
FIGS. 6 and 7 depict the installation of the preferred typist's support in a clockwise and counterclockwise fashion, respectively.
Figure 7:
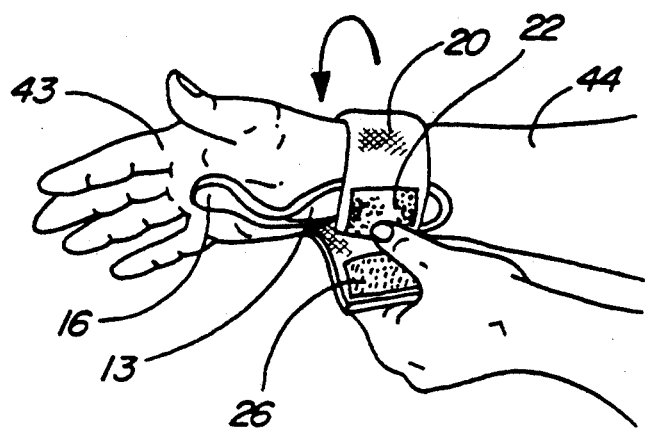

The flexible strap 20 is preferably demountably secured to the base member 12 with a mating pair of loop pile and hook pile patches 19, 27. The loop pile patch 19 is secured to the bottom surface 13 of the base member 12 with adhesive. The mating hook pile patch 27 is stitched to the inside surface 25 of the flexible strap 20 at the first end 23 thereof. The hook and loop pile patches 19, 27 collectively comprise a means for demountably securing the flexible strap 20 to the base member 12. By this arrangement, the user may variably position the flexible strap 20 relative to the base member 12 so that the flexible strap 20 wraps either clockwise or counterclockwise about the wrist as shown in FIGS. 6 and 7. The hook and loop pile patches may be reversed and other fastening means, such as snaps, are, of course, possible.

Figure 2:
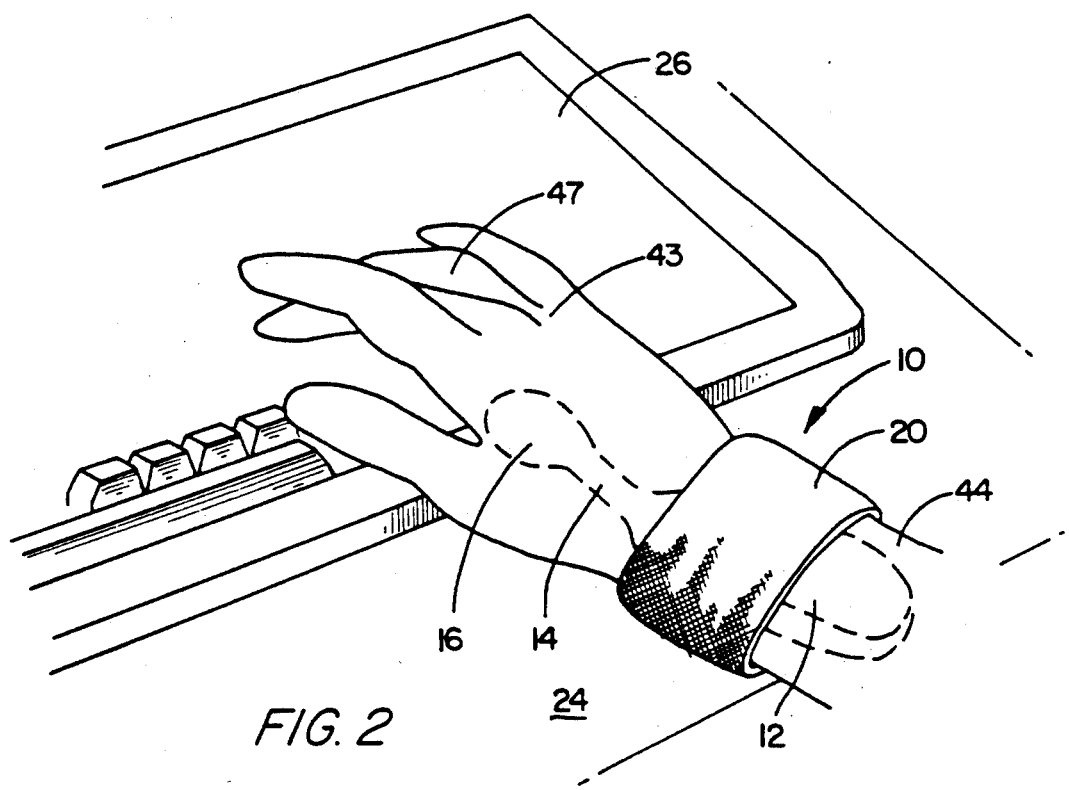
FIG. 2 is a perspective view showing a typist wearing the preferred wrist support on the right hand.
Figure 3:
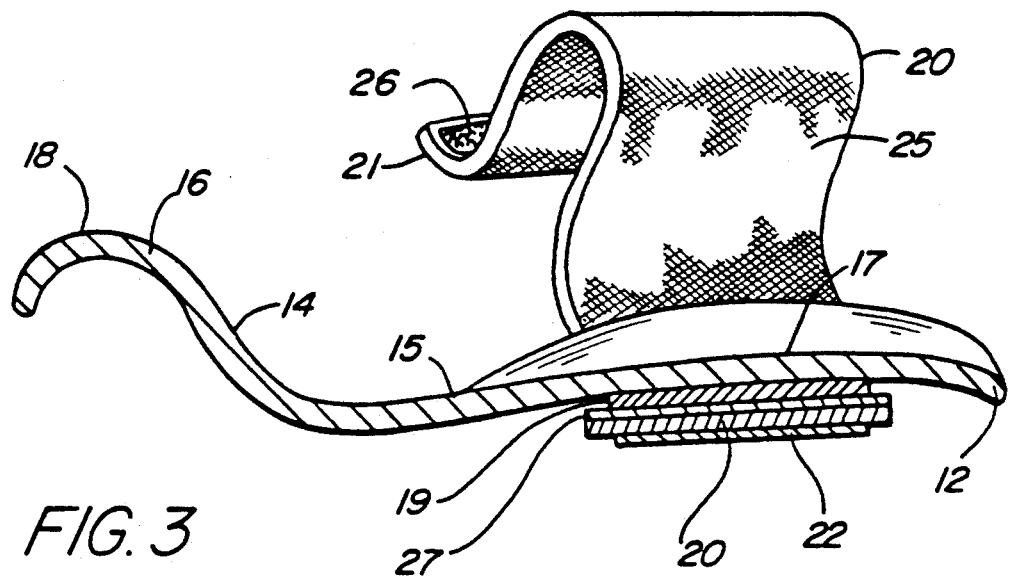
FIG. 3 is a cross-sectional view of the preferred wrist support of FIG. 1 taken along section lines 3—3.
Figure 4:
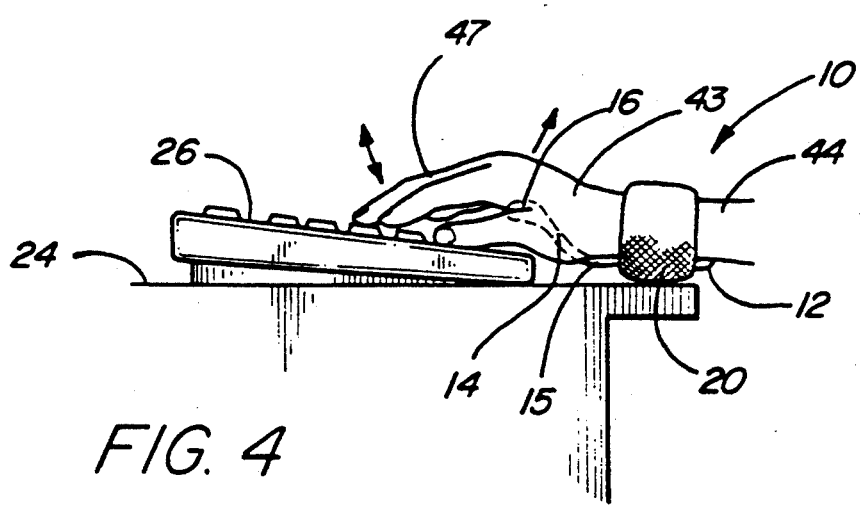
FIG. 4 is an elevational view showing how a user may pivot his or her wrist up about the front edge of base member 12.

FIG. 2 depicts the use of the preferred wrist support 10 according to the present invention. As shown, a typist's right hand 43 is supported from the underside by a wrist support 10. The wrist support 10 is most often used by someone who types with their hands elevated above the keyboard and not resting on the work surface. The wrist support 10 allows the user to relax his or her hand slightly due to the palm resting on the support member 16 and thereby transferring the load back to the wrist where it may be spread out on the surface of the base member 12. The typist may also rest his or her wrist 44 on a work surface 24. In either case, the support member 16 of the wrist support 10 fits underneath and support the user's palm to maintain a neutral wrist position to help prevent stress and fatigue. The typist's hand 43 is supported at the palm from below by the support member 16. Nonetheless, the typist's fingers 47 may move up and down and backwards and forward without restriction. By this novel arrangement, the typist is provided with increased comfort without loss of keying speed.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A wrist support for a typist comprising:
   an elongated base member having substantially parallel upper and lower surfaces of curved cross section perpendicular to an elongate axis thereof such that the upper surface comfortably wraps partially around the typist's wrist and such that the typist may pivot the lower surface of the base member from side to side on a work surface, said lower surface being substantially flat along the elongate axis of the base member such that the typist is inhibited from pivoting the base member back and forth on the work surface;
   an arm extending forward from a front edge of the base member;
   a substantially hemispherical support member attached to a distal end of the arm and having an upper curved surface of a diameter that is large enough to comfortably support the typist's palm, but small enough so that the user may pivot his or her fingers up or down, backwards and forwards; and
   means for detachably securing the base member to a user's wrist with the substantially hemispherical support member being positioned beneath the user's palm to thereby support the user's palm but not unduly restrict movement of the user's palm and fingers.

2. The wrist support of claim 1 wherein the means for detachably securing comprises a flexible strap extending from a bottom surface of the base member, said flexible strap having a loop pile patch attached to one side and at one end thereof and a hook pile patch attached to the other side and at the other end thereof, whereby the hook and loop pile patches may engage one another when the flexible strap is wrapped around the typist's wrist.

3. A wrist support for a typist comprising:
   a base member, an upper surface of the base member having a concave shape for wrapping partially around the typist's wrist and a lower surface of the base member having a convex shape so that the typist may pivot his or her wrist from side to side on a work surface;
   means for detachably securing the base member to the typist's wrist;
   an arm extending forward from a front end of the base member, a distal end thereof being positioned beneath the typist's palm;
   a substantially hemispherical appendage attached to the distal end of the arm, the substantially hemispherical appendage having an upper surface of a diameter suitable for supporting the typist's palm without unduly restricting movement of the typist's palm or fingers.

4. The wrist support of claim 3 wherein the means for detachably securing comprises a flexible strap extending from a bottom surface of the base member, said flexible strap having a loop pile patch attached to one side and at one end thereof and a hook pile patch attached to the other side and at the other end thereof, whereby the hook and loop pile patches may engage one another when the flexible strap is wrapped around the typist's wrist.

5. The wrist support of claim 4 further comprising means for demountably securing the flexible strap to a bottom surface of the base member.

6. The wrist support of claim 5 wherein the means for demountably securing comprises:
   a hook pile patch attached to the bottom surface of the base member; and
   a loop pile patch attached to the flexible strap at an end thereof, whereby the flexible strap may be oriented relative to the base member if desired.

7. A wrist support for a typist comprising:

a thin elongated base member having an upper surface and a lower surface, the base member having a curved cross section such that the lower surface may pivot from side to side on a work surface and such that the upper surface wraps partially around the typist's wrist;

a flexible strap extending from the lower surface of the base member, said flexible strap having a loop pile patch attached to one side and at one end thereof and a hook pile patch attached to the other side and at the other end thereof, whereby the hook and loop pile patches may engage one another when the flexible strap is wrapped around the typist's wrist;

an arm having a distal end and extending forward from a front end of the base member, the arm extending upward relative to an axis of the base member; and a substantially hemispherical support member attached to the distal end of the arm and having a smooth convex upper surface of a diameter suitable for comfortably supporting the typist's palm at a desired height relative to the typist's wrist without unduly restricting movement of the typist's palm or fingers.

* * * * *